US012758299B2

(12) United States Patent
Batchelor et al.

(10) Patent No.: US 12,758,299 B2
(45) Date of Patent: Oct. 13, 2026

(54) TISSUE THERAPY ENERGY DELIVERY AT A TARGET PRESSURE

(71) Applicant: GYRUS ACMI, INC., Westborough, MA (US)

(72) Inventors: Kester Julian Batchelor, Mound, MN (US); Teo Heng Jimmy Yang, Heath (GB); John Mensch, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 1000 days.

(21) Appl. No.: 17/929,485

(22) Filed: Sep. 2, 2022

(65) Prior Publication Data

US 2023/0127877 A1 Apr. 27, 2023

Related U.S. Application Data

(60) Provisional application No. 63/270,709, filed on Oct. 22, 2021.

(51) Int. Cl.
*A61B 18/14* (2006.01)
*A61B 18/00* (2006.01)

(52) U.S. Cl.
CPC .......... *A61B 18/1445* (2013.01); *A61B 18/14* (2013.01); *A61B 2018/00077* (2013.01); *A61B 2018/0063* (2013.01); *A61B 2018/1465* (2013.01); *A61B 2018/1467* (2013.01)

(58) Field of Classification Search
CPC .. A61B 2018/00077; A61B 2018/0063; A61B 18/14; A61B 18/1442; A61B 18/1445; A61B 18/1447; A61B 2018/145; A61B 2018/1452; A61B 2018/1455; A61B 2018/1465; A61B 2018/1467
See application file for complete search history.

(56) References Cited

U.S. PATENT DOCUMENTS 7,803,156 B2 9/2010 Eder et al.
2004/0143263 A1* 7/2004 Schechter ............ A61B 17/122 606/51
2005/0021027 A1* 1/2005 Shields .............. A61B 18/1445 606/51
2007/0213711 A1* 9/2007 Eder .................. A61B 18/1442 606/51
2017/0065331 A1* 3/2017 Mayer ................ A61B 18/1482
(Continued)

FOREIGN PATENT DOCUMENTS

EP 1991150 B1 5/2013

*Primary Examiner* — Bradford C. Blaise
(74) *Attorney, Agent, or Firm* — Schwegman Lundberg & Woessner, P.A.

(57) ABSTRACT

This document describes an end effector assembly of a medical device. The end effector assembly can include a jaw assembly including a first jaw member and an opposing second jaw member that can be pivotably coupled to the first jaw member at a fulcrum. The jaw assembly can be movable between a first position and a second position. An electrode can be arranged on an inner surface of the first jaw member or the second jaw member. The electrode can include a plurality of segments, such as can be arranged to be sequentially extending outward in a row away from the fulcrum. The segments can be spaced-apart from each other and individually deformable.

22 Claims, 8 Drawing Sheets

(56) References Cited

U.S. PATENT DOCUMENTS

| | | | | |
|---|---|---|---|---|
| 2017/0348043 | A1 | 12/2017 | Wang et al. | |
| 2019/0151010 | A1 | 5/2019 | Batchelor et al. | |
| 2021/0153927 | A1 | 5/2021 | Ross et al. | |
| 2021/0196307 | A1* | 7/2021 | Shelton, IV | A61B 18/1442 |
| 2021/0196334 | A1* | 7/2021 | Sarley | A61B 17/320092 |
| 2021/0196335 | A1* | 7/2021 | Messerly | A61B 18/00 |
| 2021/0196346 | A1* | 7/2021 | Leuck | A61B 17/320092 |
| 2022/0015823 | A1* | 1/2022 | Wilson | A61B 18/1445 |

* cited by examiner

TISSUE THERAPY ENERGY DELIVERY AT A TARGET PRESSURE

CLAIM OF PRIORITY

This application relates claims priority to U.S. Provisional Application Ser. No. 63/270,709, filed on Oct. 22, 2021, which is incorporated by reference herein in its entirety, and the benefit of priority of which is claimed herein.

TECHNICAL FIELD

This document pertains generally, but not by way of limitation, to systems and methods including end effectors of medical devices. In particular, this document relates to devices and methods for treating blood vessels or other tissue.

BACKGROUND

Various different types of energy, e.g., radio frequency (RF) or other electromagnetic energy, plasma energy, or ultrasound energy can be used for vessel sealing, tissue cutting or cautery, tissue ablation, or tissue coagulation, among other things, alone or in combination with mechanical energy delivery (e.g., using a sharp cutting instrument) or manipulation (e.g., using a forceps). Many types of monopolar and bipolar energy devices exist for different surgical purposes. For example, an energy delivery device ("energy device") can include a forceps that can be used for laparoscopic surgery. The forceps can perform delicate movements inside a patient and can include a gripping assembly and/or a cutting assembly. Further, the forceps can use electrical energy in the gripping assembly. Electrosurgical sealing forceps can further include or use an energy device such as RF, ultrasonic, and microwave vessel sealing devices. The forceps can clamp tissue, and elastin or collagen of the clamped tissue can be melted by the energy device such as can seal the tissue.

For example, jaws located at a distal end of a forceps can be actuated via elements at a handpiece of the forceps to cause the jaws to open and close and thereby engage the vessel or other tissue. Forceps can also include an extendable and retractable blade, such as blades that can be extended distally between a pair of jaws.

Energy devices, such as RF, ultrasonic and microwave vessel sealing devices, require a certain amount of jaw pressure to compress the tissue to create good seals with low thermal margins. Bipolar electrosurgical sealing forceps can employ a pair of jaws with RF energy to coagulate a vessel and further employ a moveable cutting blade to cut the sealed vessel after coagulation.

SUMMARY

Some forceps devices can require a high jaw force to compress the vessel tissue for desired sealing results. The high jaw force can cause unwanted tissue damage, since, for example, the jaw force requirements for large vessels and small vessels are different.

The present inventors have recognized, among other things, that tissue treatment procedures using energy delivery can benefit from improvements including reduced procedure time, reduced complications from treatment, and reducing the requisite skill level of the surgeon or other practitioner performing the procedure, such as to help reduce or avoid the need for surgical "tricks" or techniques to accommodate changing conditions at a target site during the procedure. For example, an approach to electrosurgery can include or use an electrosurgical device with a radio frequency (RF) or other electromagnetic energy delivery system for changing a force applied at a target site based on a tissue characteristic such as, e.g., vessel size. For example, a challenge of such approaches for energy delivery can include 'tissue popping'. Such tissue popping is a phenomenon in which steam generated within the tissue exits, e.g., from between forceps jaws, applying mechanical pressure and electrical energy together, at such speed that it can cause damage to the vessel wall including at one or more locations that can be away from the target vessel sealing site. It can be difficult to avoid tissue popping using, for example, a large-jawed energy device since such a device can tend to apply a significantly different force to a smaller vessel than a force applied to a larger vessel with similar operation of the large-jawed energy device.

This document describes an end effector assembly of a medical device. The end effector assembly can include a jaw assembly including a first jaw member. A second jaw member can be pivotably coupled to the first jaw member at a fulcrum. The jaw assembly can be movable towards a first position where the first and second jaw members can be opposing and spaced apart from each other. Also, the jaw assembly can be movable towards a second position where the first and second jaw members can be positioned closer to each other than in the first position. An electrode can be arranged on an inner surface of the first jaw member or the second jaw member. The electrode can include a plurality of segments, such as extending outward, and arranged in a row, away from the fulcrum. For example, the plurality of segments can include a first segment, such as with a portion of the first segment configured to deform or move in a direction away from an opposing jaw when a tensile force exceeding a specified first threshold force is present at the first segment.

In an example, the first segment can include a first compression feature configured such that a strain from the tensile force localizes disproportionately within the first segment at or near the first compression feature such that the portion of the first segment deforms in a direction away from the opposing jaw. For example, the compression feature can include a necking feature, a serration, an opening, a spring, a tapered region, or a combination thereof.

DETAILED DESCRIPTION

Figure 1A:
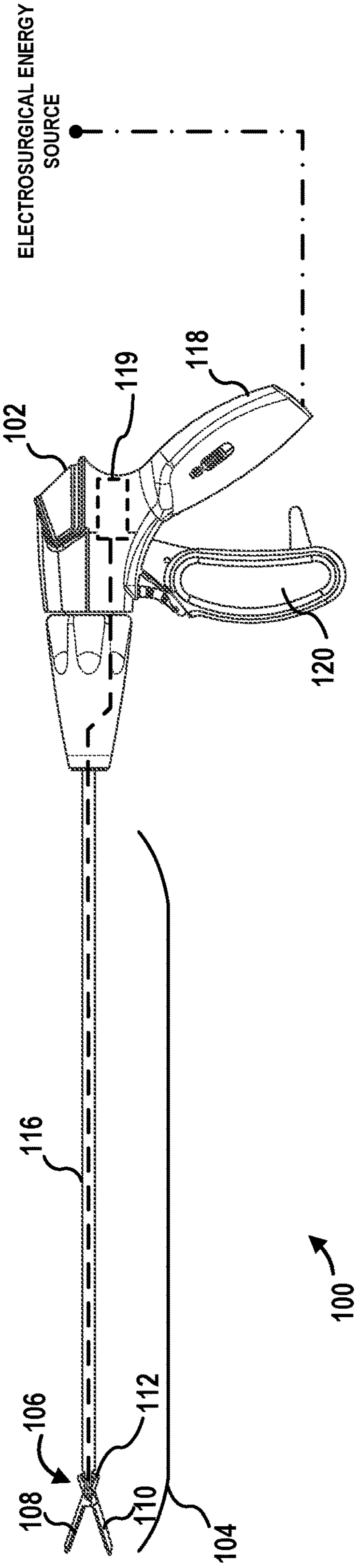
FIG. 1A depicts an example of an electrosurgical system.

This document is generally related to medical devices, such as surgical instruments for treating tissue. In an approach to tissue treatment an energy device, such as radio frequency (RF), ultrasonic, and microwave vessel sealing devices, can be used as a part of an electrosurgical sealing forceps. An end effector assembly, such as including a forceps, can provide a desired jaw pressure such as to compress the tissue for electrosurgical sealing. The energy devices can be used such as to apply energy to treat one or more tissue components, e.g., collagen or elastin of the tissue, and the heated or melted components can be used such as to seal to the tissue. Certain electrosurgical sealing forceps can also include a cutting element as part of the end effector, such as a stationary or moveable cutting blade to cut the sealed vessel. Such devices can use a relatively high jaw closure force to compress the vessel tissue for sealing. A problem with this approach, however, that an undesired jaw closure force can cause unwanted tissue damage during the procedure if the tissue is not held at an appropriate target tissue pressure. For example, an appropriate target pressure can vary based on the surface area the jaws is filled with tissue, and a range of variance can be relatively large for jaw devices capable of compression forces of greater than about 65 newtons (N). Herein, the term “about” is used to connote a margin of error of between plus or minus 10% of the reference value. It can be desirable to deliver a compression force at a particular pressure between about 40N and about 70N of force, such as about 68N of force. In perhaps more preferred examples for different sized devices, it can be desirable to deliver a compression force at a particular pressure between about 35 to 60 N of force for smaller devices, and 50 to 75 Newtons of force for larger devices. Providing such an appropriate target tissue pressure can be challenging for users, for example, if the region between the jaws is not filled with tissue. In such a case, the closure force needed from the end effector to supply the target tissue pressure can vary based on the amount of tissue is in contact with a contact surface area of the jaws. For instance, at a fixed closure force in a case in which the jaws compress a relatively small amount of tissue, a greater tissue pressure is supplied than in a case in which the jaws compress a relatively large amount of tissue at the same fixed closure force. Also, providing the desired tissue pressure can be challenging for users due to varying tissue thickness, morphology, size, volume, density, composition, moisture content, and the like. Generally, the “target tissue pressure” can refer to relatively small range of acceptable pressures for the procedure and supplying the target tissue pressure can be significant such as for a user to perform a successful procedure. If too little closure force is applied, the tissue is compressed at too small of a tissue and the resultant seals created can be very low in their ‘burst pressure’ (e.g., the blood pressure required to prevent the created seal from breaking). This is because the ‘glue’ created from the melted elements of the vessels such as the collagen, is not squeezed together sufficiently. This insufficient pressurization of the glue can result in a weakness at the pressure-treated joint interface and results in poor seals. If too great of closure force is applied, the tissue pressure is too great and, irrevocable tissue damage can occur such as tearing and ripping of the tissue. Also, if too great of closure force is applied, the tissue pressure is too great and, tissue popping can occur when the steam generated within the tissue while applying energy is trapped between the jaws at the high pressure until the jaws are released following the procedure. At this point, the steam within the walls of the vessel can escape at a high velocity and can damage surrounding tissue. This can result in behind-the-seal weaknesses that can later burst during times of patient recovery from anesthesia or post-operatively (due to the increase of a patient’s blood pressure meeting the particular blood pressure level within the vessel that causes failure at the weakened location of the “sealed” blood vessel).

The present inventors have recognized, among other things, that creating a tissue treatment system that can provide a variable closure force based on the amount of tissue along the contact area of the jaws, can help a user achieve the target tissue pressure between the jaws during energy delivery treatment, such as for vessel sealing.

Figure 1B:
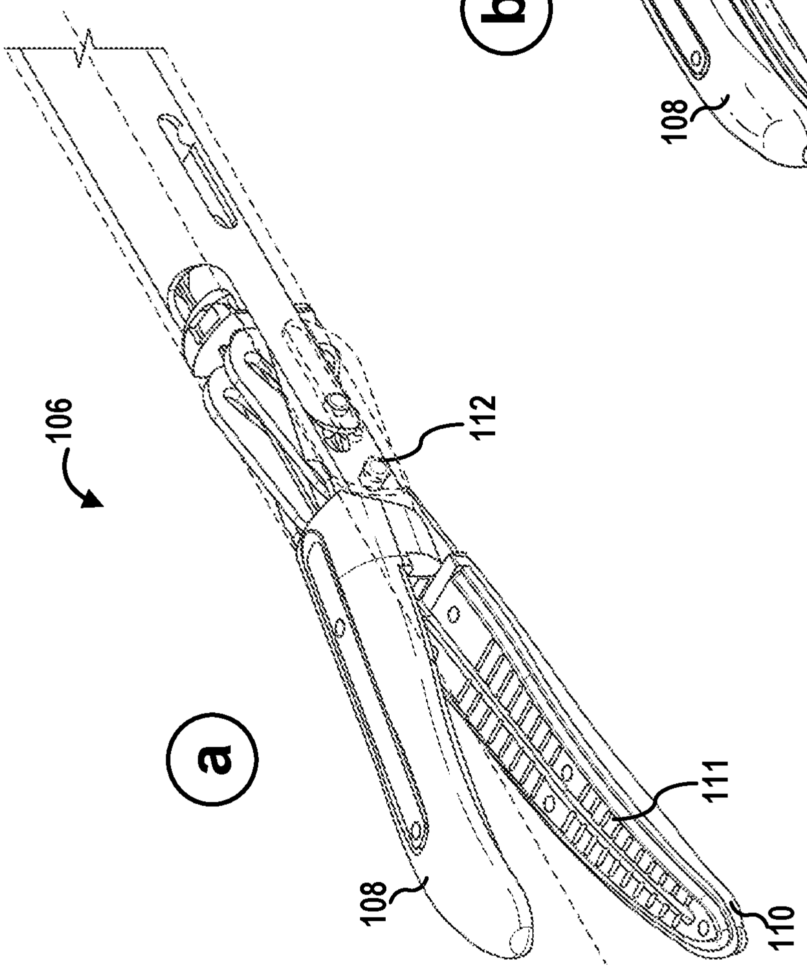
FIG. 1B depicts an example of an end effector assembly.
Figure 1C:
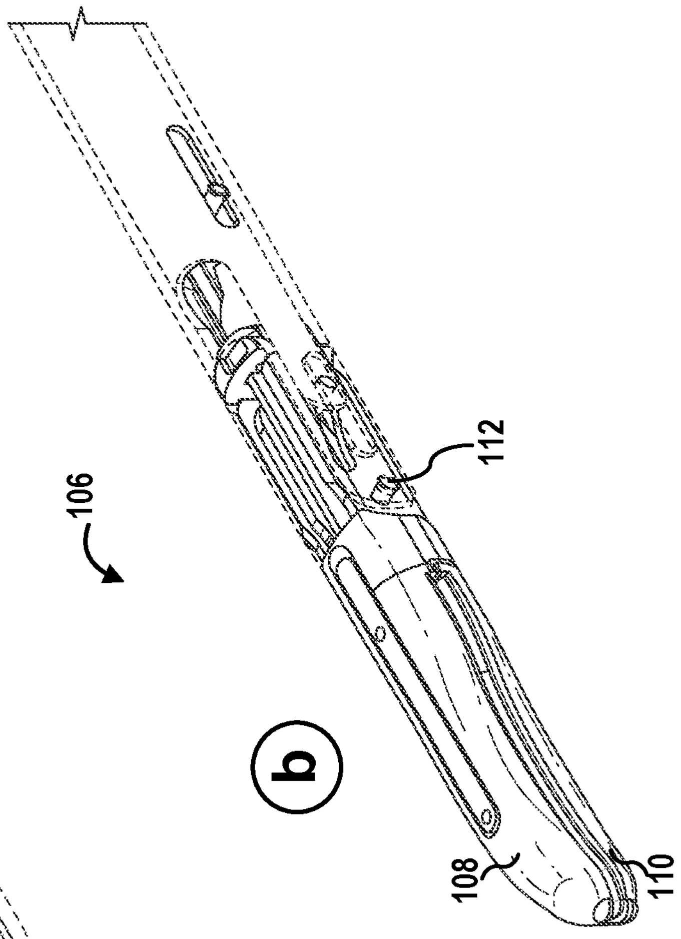
FIG. 1C depicts an example of an end effector assembly.

FIG. 1A, FIG. 1B, and FIG. 1C illustrate an example of an electrosurgical system 100. The electrosurgical system 100 can include or use a medical device 102 having an end effector assembly 104. The system 100 can be configured to deliver a tailored energy output to a variety of devices. For example, the system 100 can provide tailored waveforms to one or more electrodes, such as at least one active electrode 111 (electrode 111 depicted in FIG. 1D). Such tailored energy output can be used to treat the tissue, such as to seal, cut, ablate, fulgurate or desiccate, among other effects. In an example, the end effector assembly 104 can apply between about 20 joules per second (J/s) and about 40 (J/s), such as approximately 30 (J/s), to the tissue. In an example, such application of the energy to the tissue can include applying a jaw temperature of the end effector assembly 104 being within a range between about 120° Celcius (° C.) and about 150° C. The end effector assembly 104 can include both an active electrode and a return electrode. However, the device does not have to be a forceps, and need not be bipolar, but can employ monopolar waveforms and other types of devices. For example, an active electrode of a device can be used in conjunction with a remote return electrode, such as, but not limited to a return electrode pad. The medical device 102 can be electrically couplable to an electrosurgical energy source, such as can include a generator providing a radio frequency (RF) electrosurgical signal, an ultrasound (UT) electrosurgical signal, or a microwave (MW) electrosurgical signal.

Furthermore, the tailored energy outputs described herein can be used in systems that deliver any type of energy output that is compatible with a particular end effector or device. For example, tailoring an energy output can include tailoring the ultrasonic energy or radiofrequency energy delivered by to or by an ultrasonic forceps, or tailoring the thermal energy delivered to or by forceps or other device for one or more treatments such as cutting, sealing, coagulation, ablation, desiccation, fulguration, or the like.

The end effector assembly 104 can include or use a jaw assembly 106. The jaw assembly 106 can include a first jaw member 108 and a second jaw member 110. The second jaw member 110 can be pivotably coupled to the first jaw member 108 about a pivot axis or other pivot point 112. One or more drives 119 can be included or used in the device 102, such as housed within the hand piece 118 and mechanically coupled to the end effector assembly 104. Also, one or more drives 119 can be included at or near the distal end of the assembly 104 such directly driving the jaw assembly 106. For example, the drive 119 can include a mechanism for electrically, mechanically, pneumatically, or hydraulically transferring energy applied to an actuator 120 to operate the jaw assembly 106.

FIG. 1B and FIG. 1C shows an example in which the jaws 108 and 110 of the jaw assembly 106 can be movable between a first position a, in which the first and second jaw members 108 and 110 are spaced apart from each other and a second position b, in which the first and second jaw members 108 and 110 are positioned closer to each other than in the first position a.

Figure 1D:
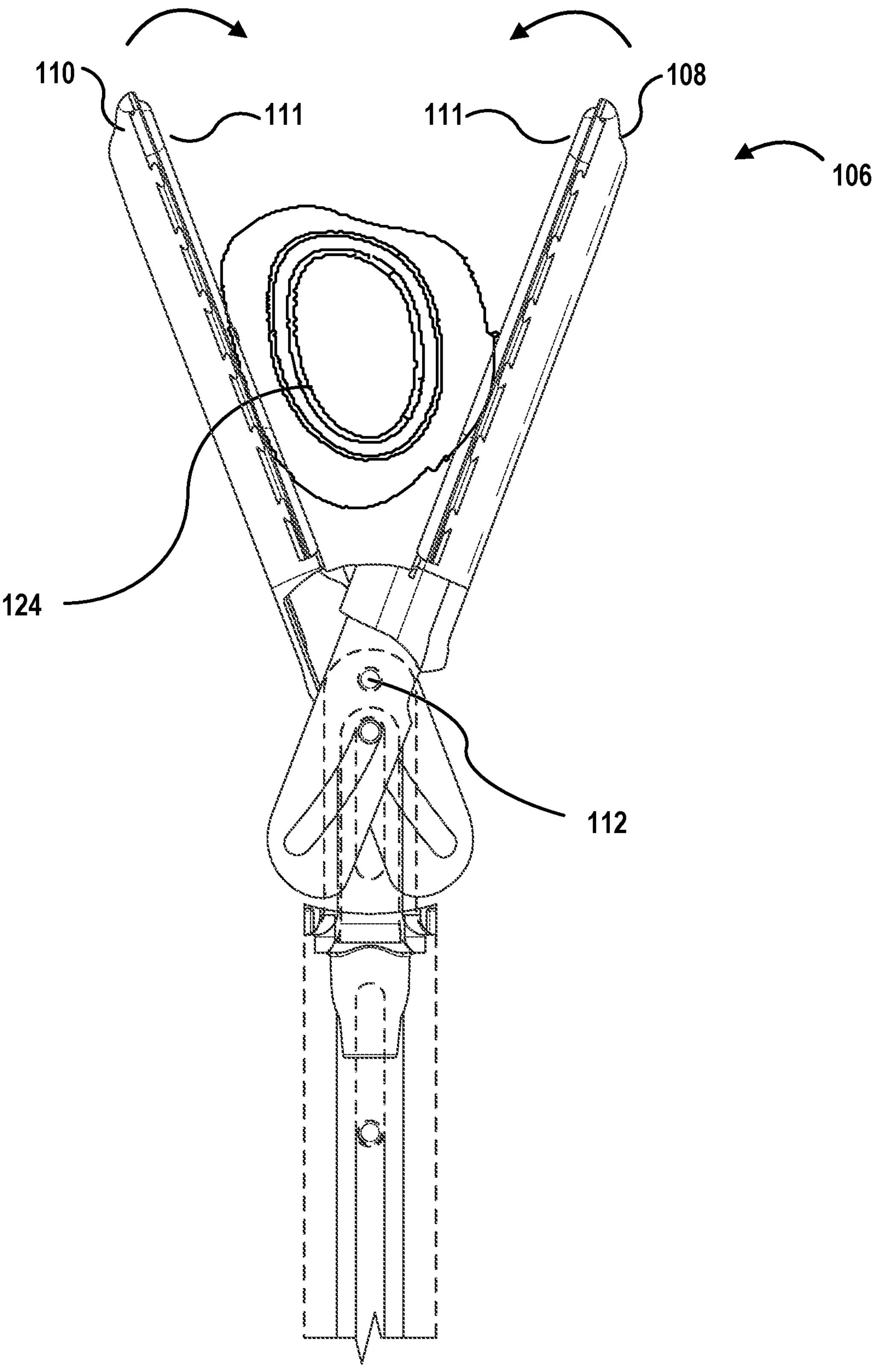

FIG. 1D shows an example in which when the first and second jaw members 108 and 110 are moved towards the second position b, the end effector assembly 104 can compress a blood vessel or other target object 124, such as a part of a body, an anatomical feature, tissue, veins, arteries, or a combination thereof of a human or animal subject. In so doing, one or more electrodes 111 on the first jaw member 108 can be moved towards the second jaw member 110. Also, two electrodes 111 arranged on the first jaw member 108 and the second jaw member, respectively, can be moved closer to each other. In an example, the end effector assembly 104 can be used in the system 100 such as to compress one or more of lymphatics, tissue pedicles, arteries, and veins, such as with a diameter or similar cross-sectional dimension ranging from about 0.5 mm to about 7 mm. Herein, a diameter of a vessel can refer to either of a measured diameter or an average diameter along a length of interest of a vessel of interest. Also, vessels described herein need not conform to exact circles in cross-section, the vessel diameter can also refer to a minimum diameter, maximum diameter, or calculated diameter obtained from one or more measurements. In an example, the end effector assembly 104 can be used in the system 100 such as to compress lymphatics or arteries with a diameter or other similar cross-sectional dimension greater than 7 mm. At least one of the first and second jaw members 108 and 110 can include electrodes that can be adapted such as to be electrically connected to an electrosurgical energy source, such as to provide current that can be passed through the electrodes of the end effector assembly 104. For example, a therapy current can be passed from the first jaw member 108 to the second jaw member 110 when tissue is located within the jaw and the therapy current can coagulate blood, cauterize, cut, or a combination thereof. Returning to FIG. 1A, the medical device 102 can include parts employed to perform the recited functions and can include an elongated or other shaft 116 (e.g., a tubular member, a hollow tube, or an assembly of tubes), a hand piece 118, one or more operable mechanisms used to manipulate the shaft 116 or to actuate the end effector assembly 104, such as the actuator 120, or a combination thereof. The hand piece 118 can be an assembly of parts or housing structures capable of forming a hand piece 118 structure with a cavity. In an example, the shaft 116 and the end effector assembly 104 can be included with or mounted to the end of a robotic arm such as to permit robotic stabilization, positioning, manipulation, and operation, instead of being hand-held by a user grasping the hand piece 118.

Figure 2A:
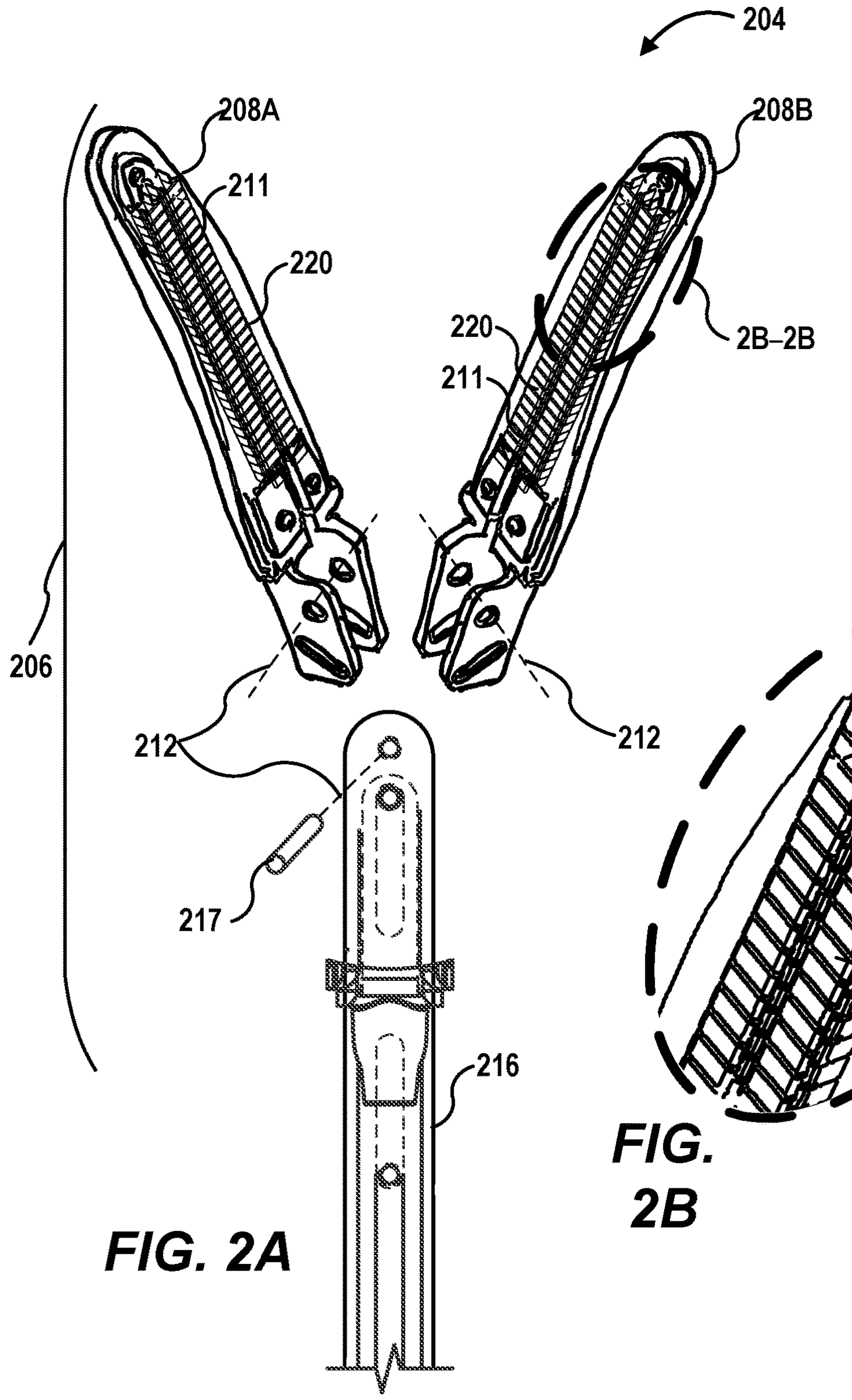
FIG. 2A is an exploded view of an example of an end effector assembly.
Figure 2B:
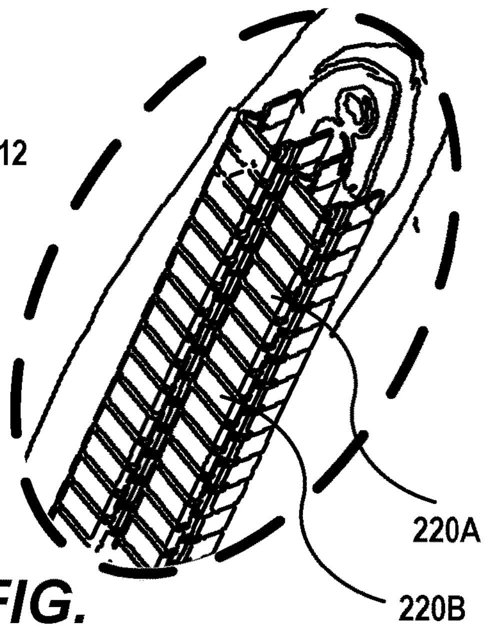
FIG. 2B is a detailed view of the example of an end effector assembly depicted in FIG. 2A.

FIG. 2A and FIG. 2B depict an example of an end effector assembly. An end effector assembly 204 can include or use a jaw assembly 206 including a plurality of jaw members 208. The plurality of jaw members 208 can be pivotably coupled to a shaft 216 such as via a pin 217 inserted through the distal end of the shaft 216 and through at least one of the plurality of jaw members 208 along a pivot axis 212. Here, the pivot axis 212 defines a fulcrum. In an example, as depicted in FIG. 2A, an individual jaw member can include or use a plurality of deformable segments 220 arranged such as to help provide a controlled closure force application regardless of a tissue contact area with the jaw assembly 206. Herein, "deformable" refers to the ability for at least a portion of the segment to change a shape, size, orientation, or configuration upon receipt of a certain pressure. In other words, deformable generally refers to an ability of at least a portion of the segment to change shape during normal operation of a jaw device without breaking. In an example, the deformable segments 220 can be resiliently deformable, such as able to recover or revert to a prior shape, size, orientation, or configuration upon release of the certain pressure. Deformable can also be defined as substantially elastic deformation, such as deformable without substantial plastic deformation to the degree that would affect the function and life of the device (e.g., intended or normal function and life of the device).

Here, the plurality of deformable segments 220 can selectively apply a maximum force locally to a single area of the jaw. This can help allow the jaw to provide a force per area and help achieve an appropriate target tissue pressure. In an example, at least one of the plurality of deformable segments can also be included as part of the electrode 211 for delivering electrosurgical energy to the target site. In an example, the end effector assembly 204 includes a plurality of deformable segments 220, such as sequentially extending outward in a row away from the fulcrum.

An individual jaw member 208 can include or use an electrode 211, such as arranged on an inner surface of the first jaw member 208A or the second jaw member 208B. While depicted in FIG. 2A as having two jaw members 208A and 208B with respective pluralities of deformable segments 220, similar end effector assemblies described herein can include only one jaw member having deformable segments 220 and arranged opposite another jaw member without similarly deformable segments 220. For example, a second jaw member 208B can include a grip plate without deformable segments, i.e., the grip plate not sized, shaped, and arranged to deform during normal use within a forceps during tissue compression.

As depicted in in the detail view in FIG. 2B, an individual jaw member 208 can also include or use a first segment 220A, and the first segment 220A can be arranged such as to deform or move in a direction away from an opposing jaw when a tensile force exceeding a specified threshold force is present at the first segment 220A. The first segment 220A can be arranged, sized, and shaped such as to deform or move in a direction away the opposing jaw when a tensile force exceeding a specified threshold force is present at the first segment 220A. An individual jaw member 208A or 208B can also include a second segment 220B, such as longitudinally spaced apart from the first segment 220A.

Not all of the plurality of deformable segments 220 need have the same deflection force against a force of deformation. For example, certain areas of an individual jaw member 208A or 208B can deform when subject to a lower force or a higher force than another area of the jaw member. This can help allow a physician to utilize specific areas of the individual jaw 208A or 208B such as for specific tasks. For example, a specified first threshold force at the first segment 220A can be different than a specified second threshold force at the second segment 220B. For example, a specified first threshold force at the first segment 220A can be greater than a specified second threshold force at the second segment 220B. In an example, the first segment 220A can be arranged such as to deform more than the first segment 220B upon being subject to the same tensile force.

Figure 3B:
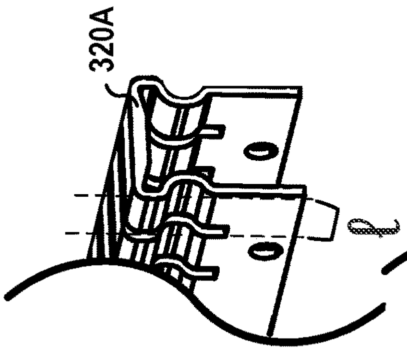
FIG. 3B depicts an example of a grip plate of a jaw member including a plurality of deformable segments.
Figure 3C:
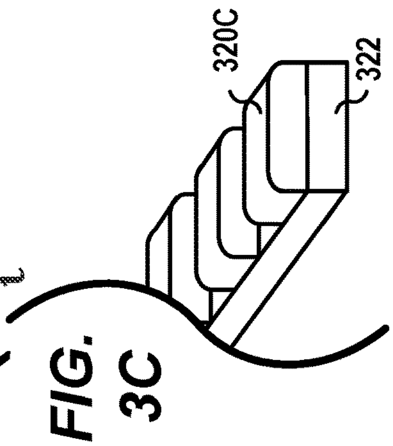
FIG. 3C depicts an example of a grip plate of a jaw member including a plurality of deformable segments.
Figure 3D:
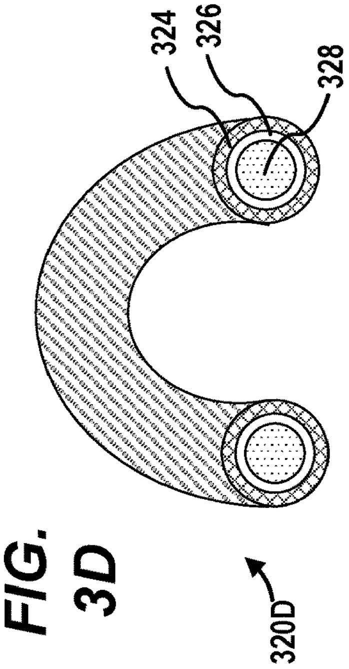
FIG. 3D depicts an example of a segment of a grip plate for use in a jaw member.
Figure 3A:
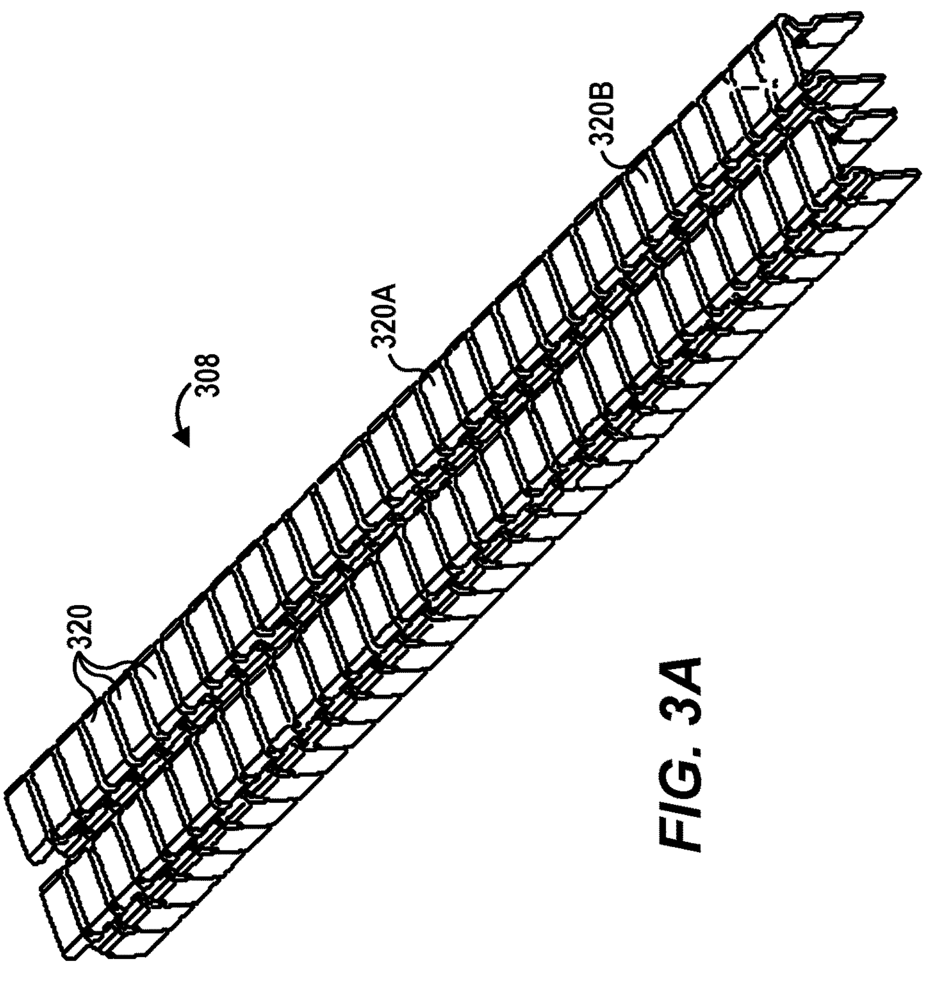
FIG. 3A depicts an example of a grip plate of a jaw member including a plurality of deformable segments.

FIG. 3A, FIG. 3B, and FIG. 3C depict an example of a grip plate of a jaw member including a plurality of deformable segments. Similar to that previously described, an individual jaw member can include or use a grip plate 308 including at least one segment 320. For example, at least a portion of a first segment 320A can be arranged such as to deform or move in a direction away from an opposing jaw when a tensile force exceeding a specified threshold force is present at the first segment 320. The first segment 320 can be included as part of an electrode for delivering electrosurgical energy to the target site. In an example, the end effector assembly includes a plurality of segments 320, such as sequentially extending outward in a row away from the fulcrum. For example, the first segment 320A included in the plurality of segments 320 can be configured to deform or move in a direction away the opposing jaw when a tensile force exceeding a specified second threshold force can be present at the first segment 320A. Also, a second segment 320B can be longitudinally spaced apart from the first segment 320A. In an example, a specified first threshold force at the first segment 320A can be different than a specified second threshold force at the second segment 320B. For example, a specified first threshold force at the first segment 320A can be greater than a specified second threshold force at the second segment 320B. In an example, the first segment 320A can be arranged such as to deform more than the first segment 320B upon being subject to the same tensile force.

FIG. 3B depicts an example of a plurality of segments of a jaw member. An individual segment 320A of the plurality of segments 320 can have a length (l) between about 0.2 mm and about 10 mm. The individual segment 320A can help allow a predetermined force to be applied to the target tissue and subsequently to deflect, give, or otherwise reduce the total amount of the jaw closure force, from being transmitted to a single area within the jaws. For example, this can help allow the end effector assembly to apply a closure force of, e.g., 75N, and to transmit all 75N to the tissue when the tissue contact area of the jaw is high (i.e., a fuller jaw) but to provide a reduced force to tissue between the jaws when the tissue contact area of the jaw is low (i.e., a less-full jaw).

FIG. 3C depicts another example of a plurality of segments of a jaw member. An individual segment 320C can include or use a malleable material, such as a foam, silicone rubber, a sponge material, a deformable elastomer, or a fluid or gel material. Also, an individual segment 320C can be attached to an elastic material 322, and the segment 320C can be formed of a rigid material. In an example, a first jaw member can include a segment 320C formed of a malleable or elastic material, and the second jaw member can include a more rigid segment 320A (as depicted in FIG. 3B) arranged opposite the malleable segment 320C.

FIG. 3D depicts an example of a segment of for use in a jaw member. An individual segment 320D can include or use a malleable hydrocenter loop including a metallic layer 324, a hydrocenter tubing 326, and a hydrocenter 328. For example, the metallic layer 324 can include a mesh material, e.g., braided strands of metal such as stainless steel, copper, or aluminum. Also, the metallic layer 324 can include a row of solid or semisolid segments of metal. The hydrocenter tubing 226 can be formed of polytetrafluoroethylene (PTFE), polyvinylidene fluoride (PVDF), ethylene tetrafluoroethylene (ETFE), polyamides, copolymers of polyetheretherketone (PEEK) or other suitable materials. The hydrocenter 328 can be filled with a fluid material that is malleable or deformable when compressed, such as water or a water-based gel, in an amount to create a "hydrocenter" that can be readily compressed into a compact volume when the jaw member is bent to a desired shape.

Figure 4A:
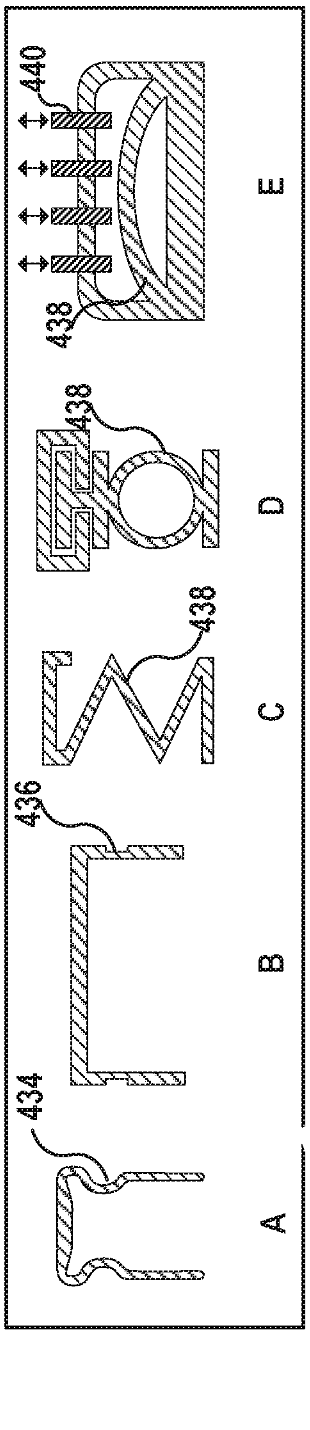
FIG. 4A depicts several example cross-sections A-E that can be included in segments described herein.
Figure 4C:
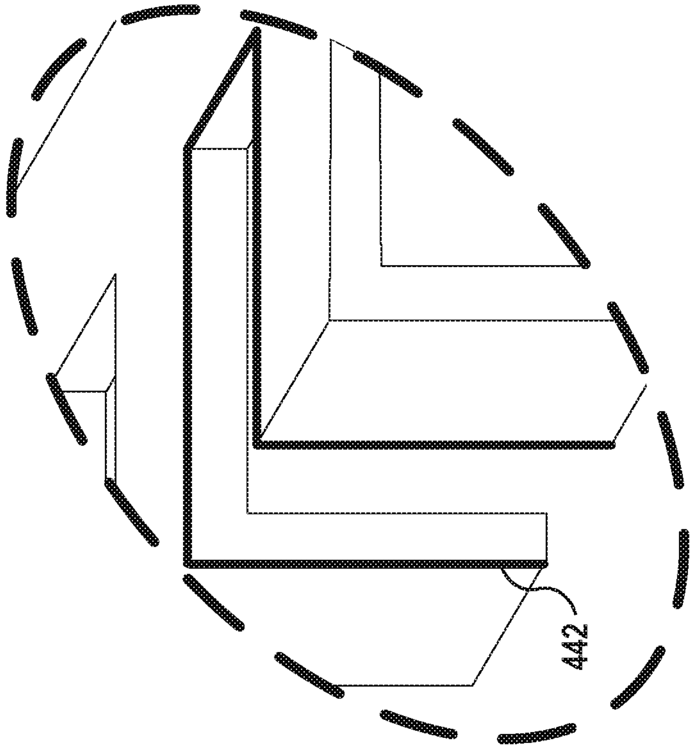
FIG. 4C depicts an example of an individual segment of a jaw member.
Figure 4B:
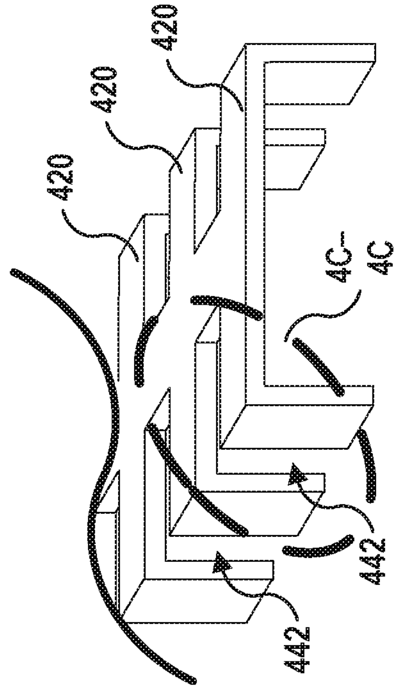
FIG. 4B depicts an example of an individual segment of a jaw member.

FIG. 4A, FIG. 4B, and FIG. 4C depict examples of an individual segment of a jaw member. FIG. 4A shows example cross-sections A-E that can be included in segments described herein. As exemplified in the various cross-sections, segments described herein can include one or more compression features. For example, as depicted in cross-section A, an individual segment can include or use one or more necking features 434. As depicted in cross-section B, an individual segment can include or use one or more serrations 436. As depicted in cross-sections C, D and E, an individual segment can include or use one or mechanical biases 438, such as a spring 438. In particular, with respect to cross-section E, one or more conductive posts 440 can be included in contact with the mechanical bias 438. In an example, the conductive post 440 can contact the target tissue and be forced towards the mechanical bias 438. In an example, the conductive post 440 can electrically conduct electrosurgical energy upon contact with the mechanical bias 438 and cease conducting the energy when contact with the mechanical bias 438 is released. The compression feature can include or use an opening or a tapered region. In an example, an individual jaw member can include or use a first compression feature e.g., located laterally outward of a second compression feature. In an example, the first and second compression features can be each configured such that a strain from the tensile force can localize at both the first and second compression can feature equally, such that the at least a portion of the first segment deforms in a direction away from the opposing jaw and maintains a substantially parallel orientation with respect to an inner face of the opposing jaw upon deformation. Also, the first and second compression features can be each configured such that a strain from the tensile force can localize at the first and second compression can feature inequally, such that the at least a portion of the first segment deforms more than a corresponding respective portion of the opposing jaw and deformation of the jaws with respect to each other is different.

Different materials, material thicknesses, and segment lengths can affect the force required to cause the mechanical bias 438 to depress and can be tuned to the specific requirements of the device, can be characterized by F=kx, where F is the applied force, k is the spring constant and x is the amount of displacement. Alternatively, "necking" or another form of reduced cross-sectional area or voids such as by drilling, stamping, punching or etching can be introduced to reduce the second moment of inertia. This is characterized by a buckling force constitutive equation:

$$P = \frac{\pi^2 EI}{L^2}$$

where P is the buckling load, E is the Young's modulus, I is the 2nd moment of area and L is the length of the column.

In an example, the compression feature limits twisting, deformation in any one direction or contact with an adjacent segment upon compression thereof. Preventing such twisting can help prevent the electrode from impeding the track of a vessel sealing device that includes a cut blade, prevent the electrode from moving closer to the tissues that are outside of the general footprint of the device, increasing 'thermal margin or tissue effect area into unwanted or unexpected areas; twisting or deforming into an adjacent segment and becoming locked or supporting itself and altering the deformation force; trapping or scissoring tissues that transverse one or more segments and damaging the tissue by cutting or not allowing a subsequent release of the tissue once the jaw has been opened.

The mechanical bias 438 can be made from a number of different materials, including polymers, elastomers or metals. In the example where the spring material is metallic, it can be formed by folding or etched, laser cut, or stamped, or any other suitable process for forming a spring, such as coiling. In some examples, the mechanical bias 438 can include a metal-based spring system that uses two springs to equalize the pressure from side to side to provide a parallel drop to the contact area of the jaw member. In other examples, the mechanical bias 438 can be located generally centrally in a lateral direction. The mechanical bias 438 can be also be located generally centrally in the lateral direction (i.e., along the length of the jaw), or can be biased towards a distal portion of the respective segment or the proximal portion of the respective segment.

One or more protection coverings 421 (e.g., layer) can be included to cover an individual segment or a plurality of segments such as to minimize or impede tissue from becoming trapped between a plurality of segments or to help provide a non-stick contact surface for contacting tissue. For example, the protection covering 421 can be formed of polymers, metals, foils and metals, for example, polycarbonate, polyurethane, polysulfone, polyethylene, polypropylene, polyimide, polyfluorocarbon, polyvinyl chloride, polyvinylidene chloride, polystyrene, poly(vinyl chloride-co-vinyl alcohol), polyamide, poly(methyl methacrylate), polyethylene terephthalate, poly(ethylene-co-vinyl acetate). For example, an additional flexible or semi flexible element can be introduced from below to fill the gaps between the segments but still allow the deflection of a single segment element.

In an example, an individual segment can be formed such as by etching or laser cutting an electrode shim and form to shape and then integrated the shim into a compliant material such as an elastomer or foam. For example, the electrode can be an array of "pads", connected through linkages from the sheet metal to form electrical continuity. In on example, the vertical linkages can be "kink" or bent to form a spring if needed. An advantage of using a compliant material is that it will give a viscoelastic property that potentially can be gentle to the tissue clamped between the jaws. This can be characterized by a combination of F=kx and also a damping effect of the compliant material, damping ratio, expressed by the formula:

$$\zeta = \frac{c}{2m\omega_n}$$

Where c=damping coefficient; m is the mass and on is the natural frequency.

In an example, an individual electrode shim can include a thickness between about 0.05 millimeters (mm) and about 1 mm. Particularly, an individual electrode shim can include a thickness between about 0.20 mm and about 0.30 mm.

Figure 5:
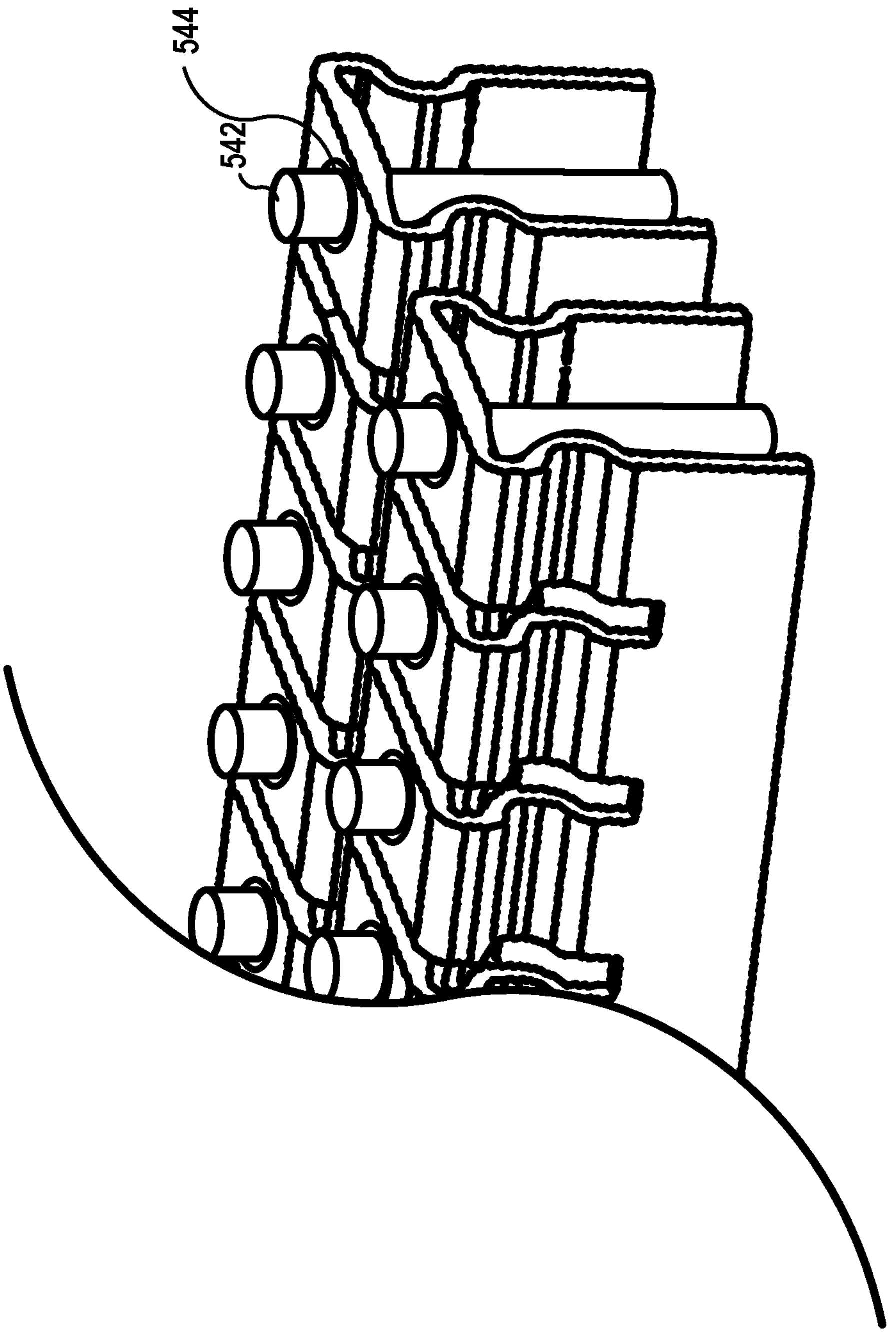
FIG. 5 is depicts an electrode component of a jaw assembly including an insulated stop element.

FIG. 4B depicts an example of a plurality of segments 420 being formed by a plurality of lateral cutouts 442 (lateral cutout 442 bolded in detail view of FIG. 4C). For example, a bar can be formed including a cross-section, such as at least one of cross-sections A-E as depicted in FIG. 4A, and then weakened by the plurality of lateral cutouts 442. For example, the plurality of lateral cutouts 442 can be machined FIG. 5 is a perspective view of the electrode component of a jaw assembly including an insulated stop element. As seen in FIG. 5, a standoff 542 can be included or used with an individual segment such as to prevent opposing jaws from electrically shorting together, when the 'standoff 542, such as an insulating stop element, can be placed on the surface of the electrode. The electrically nonconductive standoff element can extend through a cutout 544 within an individual segment. For example, the standoff 542 can protrude through an individual segment or alternatively can be arranged adjacent to an individual segment.

The standoff 542 can be conductive or insulative, while remaining arranged such as to prevent shorting from one jaw to the other. For example, a conductive stope can be at least partially surrounded by an insulative media such as to prevent it from electrically connecting on the side of the jaws on which it is insulated. In an example, an individual segment can include or use an electrically nonconductive standoff element configured to impede a first jaw member from physically contacting a second jaw member when the first and second jaw members can be moved towards each other.

Figure 6:
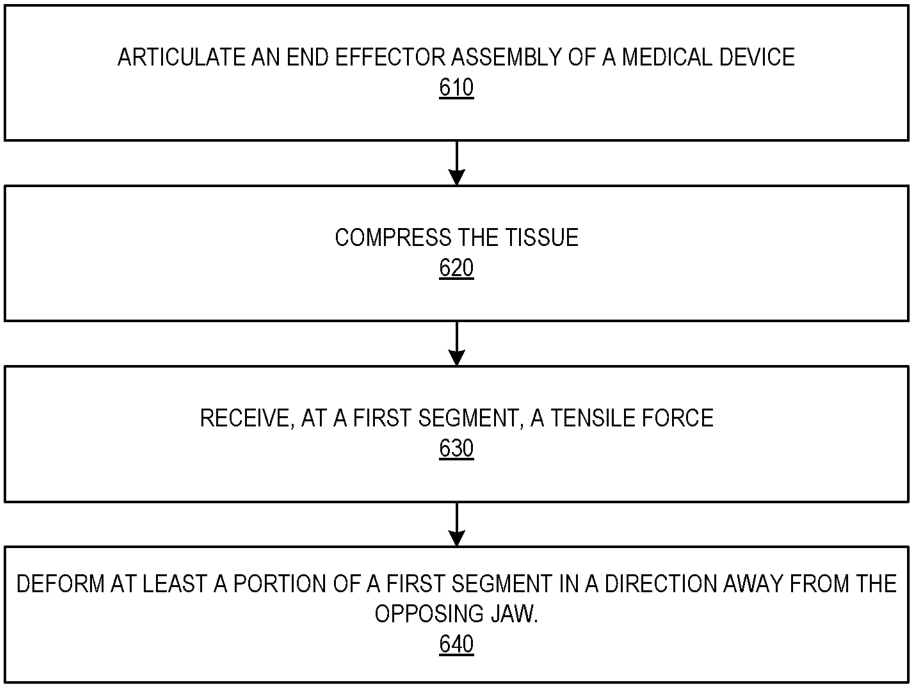
FIG. 6 is a flowchart that describes a method for applying a target pressure to a tissue, according to some examples of the present document.

FIG. 6 is a flowchart that describes an example of a method for applying a target pressure to a tissue. At 610, the method can include articulating an end effector assembly of a medical device between a first position, where first and second jaw members are spaced apart from each other, and a second position where the first and second jaw members are moved closer to each other. At 620, the method can include compressing the tissue between the first and second jaw members of the end effector assembly. At 630, the method can include receiving or applying a tensile force at a first segment of a plurality of segments included on an individual jaw member. At 640, the method can include, in response to the first tensile force exceeding a specified first threshold force, deforming at least a portion of a first segment of the plurality of segments in a direction away from an opposing jaw. The compressed tissue can contact a plurality of segments located on the first jaw assembly or the second jaw assembly.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical document. It is submitted with the understanding that it will not be used to interpret or limit the scope or meaning of the claims. Also, in the above Detailed Description, various features can be grouped together to streamline the document. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or examples, with each claim standing on its own as a separate embodiment, and it is contemplated that such examples can be combined with each other in various combinations or permutations. The scope of the invention should be determined with reference to the appended claims, along with the full scope of equivalents to which such claims are entitled.

What is claimed is:

1. An end effector assembly of a medical device, the end effector assembly comprising a jaw assembly comprising:
- a first jaw member;
- a second jaw member pivotably coupled to the first jaw member at a fulcrum wherein the jaw assembly is movable between a first position in which the first and second jaw members are opposing and spaced apart from each other and a second position in which the first and second jaw members are positioned closer to each other than in the first position; and
- an electrode arranged on an inner surface of the first jaw member or the second jaw member, the electrode including a plurality of segments extending outward in a row away from the fulcrum, each segment of the plurality of segments being physically separated from an adjacent segment of the plurality of segments by a lateral cutout extending through the electrode, the plurality of segments including:
  - a first segment configured to deform or move in a direction away from an opposing one of the first jaw member or the second jaw member, when a tensile force exceeding a specified first threshold force is present at the first segment; and
  - a second segment configured to deform or move, independently from the deformation or moving of the first segment and in a direction away from the opposing jaw member, when a tensile force exceeding a specified second threshold force is present at the second segment, wherein the second segment is physically separated from the first segment by the lateral cutout such that the first segment is independently deformable with respect to the second segment along a length of the lateral cutout.

2. The end effector assembly of claim 1, wherein the first segment includes a first compression feature configured to transmit energy received from an electrosurgical energy source to at least one of the plurality of segments.

3. The end effector of claim 1, wherein the second segment is longitudinally spaced apart from the first segment.

4. The end effector assembly of claim 1, wherein the specified first threshold force at the first segment is greater than the specified second threshold force at the second segment.

5. The end effector assembly of claim 1, wherein the first segment is configured to deform more than at least the second segment upon being subject to a same tensile force.

6. The end effector assembly of claim 1, wherein the first segment includes a first compression feature configured such that a strain from the tensile force localizes within the first segment at or near the first compression feature such that the first segment deforms in a direction away from the opposing jaw member.

7. The end effector assembly of claim 6, wherein the compression feature includes at least one of:
- a necking feature;
- a serration;
- an opening;
- a spring; or
- a tapered region.

8. The end effector assembly of claim 6, wherein the first segment includes a second compression feature configured such that a strain from the tensile force localizes disproportionately within the first segment at or near the second compression feature such that the first segment deforms in a direction away from the opposing jaw member.

9. The end effector of claim 8, wherein the first compression feature is located laterally outward of the second compression feature.

10. The end effector assembly of claim 8, wherein the first and second compression features are each configured such that a strain from the tensile force localizes at both the first and second compression features equally, such that the first segment deforms in a direction away from the opposing jaw member and maintains a substantially parallel orientation with respect to an inner face of the opposing jaw member upon deformation.

11. The end effector assembly of claim 1, wherein the first jaw member includes an electrically nonconductive standoff element configured to impede the first jaw member from contacting the second jaw member when the first and second jaw members are moved towards the second position.

12. The end effector assembly of claim 11, wherein the electrically nonconductive standoff element extends through a cutout in the first segment.

13. The end effector assembly of claim 1, comprising an electrically conductive layer covering the plurality of segments.

14. A forceps comprising:

an end effector assembly comprising:

a first jaw having a tissue sealing surface; and a second jaw having a tissue sealing surface, wherein the first jaw and the second jaw move between an open position and a closed position, wherein the tissue sealing surface of at least one of the first jaw and the second jaw includes an electrode having a plurality of individually separately compressible segments, each segment of the plurality of individually separately compressible segments being physically separated from an adjacent segment of the plurality of individually separately compressible segments by a lateral cutout extending through the electrode;

wherein the individually separately compressible segments include:

a first segment configured to deform or move when a tensile force exceeding a specified first threshold force is present at the first segment; and a second segment configured to deform or move, independently from the deformation or moving of the first segment, when a tensile force exceeding a specified second threshold force is present at the second segment, wherein the second segment is physically separated from the first segment by the lateral cutout such that the first segment is independently deformable with respect to the second segment along a length of the lateral cutout.

15. The forceps of claim 14, wherein the first jaw includes a body extending from a proximal end to a distal end of the first jaw and the electrode includes an electrode sealing surface spaced apart from the body via at least one deformable member.

16. The forceps of claim 15, wherein the electrode sealing surface is spaced apart from the body via at least two deformable members.

17. The forceps of claim 14, wherein the first segment is moveable with respect to the second segment on a same one of the first or second jaw.

18. A method for applying a target pressure to a tissue via a medical device, the method comprising:

articulating an end effector assembly of a medical device between:

a first position wherein first and second jaw members of the end effector assembly are spaced apart from each other; and a second position wherein the first and second jaw members are positioned closer to each other than in the first position; and compressing the tissue between the first and second jaw members of the end effector assembly, wherein the compressed tissue contacts a plurality of individually deformable segments located on the first jaw member or the second jaw member, each segment of the plurality of individually deformable segments being separated from an adjacent segment of the plurality of individually deformable segments by a lateral cutout;

wherein the individually deformable segments include:

a first segment configured to deform or move when a tensile force exceeding a specified first threshold force is present at the first segment; and a second segment configured to deform or move, independently from the deformation or moving of the first segment, when a tensile force exceeding a specified second threshold force is present at the second segment, wherein the second segment is physically separated from the first segment by the lateral cutout such that the first segment is independently deformable with respect to the second segment along a length of the lateral cutout.

19. The method of claim 18, comprising:

receiving or applying, at the first segment of the plurality of individually deformable segments, a first tensile force; and in response to the first tensile force exceeding the specified first threshold force, deforming at least a portion of the first segment of the plurality of individually deformable segments in a direction away from an opposing jaw member of the first jaw member or the second jaw member.

20. The method of claim 19, comprising:

receiving or applying, at the second segment of the plurality of individually deformable segments, a second tensile force; and in response to the second tensile force exceeding the specified second threshold force, deforming at least a portion of the second segment of the plurality of individually deformable segments in a direction away from the opposing jaw member.

21. The method of claim 20, wherein the specified first threshold force at the first segment is greater than the specified second threshold force at the second segment.

22. The method of claim 20, comprising:

receiving or applying, at the second segment of the plurality of individually deformable segments, a third tensile force; and in response to the third tensile force exceeding the specified first threshold force, withstanding deformation of the second segment of the plurality of individually deformable segments in a direction away from the opposing jaw member concurrent with deformation at the first segment.

* * * * *